United States Patent [19]
Clemens

[11] Patent Number: 5,340,290
[45] Date of Patent: Aug. 23, 1994

[54] DOUBLE FEED PERISTALTIC PUMP

[75] Inventor: Anton H. Clemens, Madison, Wis.

[73] Assignee: Scilog, Inc., Verona, Wis.

[21] Appl. No.: 164,429

[22] Filed: Dec. 8, 1993

Related U.S. Application Data

[63] Continuation of Ser. No. 994,148, Dec. 21, 1992, abandoned.

[51] Int. Cl.⁵ .................................................. F04B 43/12
[52] U.S. Cl. ........................... 417/477 R; 417/477 H; 417/477 J
[58] Field of Search .................. 417/474, 475, 476, 477

[56] References Cited

U.S. PATENT DOCUMENTS

| | | | |
|---|---|---|---|
| 2,818,815 | 1/1958 | Corneil | 417/477 |
| 3,137,240 | 6/1964 | Hunt . | |
| 3,138,104 | 6/1964 | Cantor . | |
| 3,447,478 | 3/1967 | Clemens . | |
| 3,597,124 | 9/1969 | Adams . | |
| 3,927,955 | 12/1975 | Spinosa et al. | 417/477 |
| 4,138,205 | 2/1979 | Wallach | 417/477 |
| 4,187,057 | 2/1980 | Xanthopoulos . | |
| 4,205,948 | 6/1980 | Jones | 417/477 |
| 4,210,138 | 7/1980 | Jess, et al. . | |
| 4,211,519 | 7/1980 | Hogan . | |
| 4,233,001 | 11/1980 | Schmid | 417/475 |
| 4,333,088 | 6/1982 | Diggins | 417/475 |
| 4,515,584 | 5/1985 | Abe, et al. . | |
| 4,519,754 | 5/1985 | Minick . | |
| 4,552,516 | 11/1985 | Stanley | 417/477 |
| 4,559,040 | 12/1985 | Horres et al. | 417/476 |
| 4,586,882 | 5/1986 | Tseng | 417/477 |
| 4,631,008 | 12/1986 | Stenner . | |
| 4,758,228 | 7/1988 | Williams | 417/477 |
| 4,813,855 | 3/1989 | Leveen et al. . | |
| 4,925,376 | 5/1990 | Kahler | 417/477 |
| 5,064,358 | 11/1991 | Calari | 417/477 |

FOREIGN PATENT DOCUMENTS

| | | | |
|---|---|---|---|
| 2132193 | 6/1971 | Fed. Rep. of Germany | 417/477 |
| 230582 | 11/1985 | Japan | 417/475 |
| 268887 | 11/1986 | Japan | 417/477 |
| 3290084 | 12/1991 | Japan | 417/477 |

*Primary Examiner*—Richard A. Bertsch
*Assistant Examiner*—Roland G. McAndrews, Jr.
*Attorney, Agent, or Firm*—Lockwood, Alex, Fitzgibbon & Cummings

[57] ABSTRACT

A peristaltic pump having a first and second shoe mechanism being slidably mounted on a pump body is provided to allow the placement of two flexible tubes therein. The pump preferably includes tube holding mechanisms to prevent the flexible tube from moving while engaged by the pump. The pump exhibits dual feed capabilities that allow the simultaneous pumping of two distinct fluids at a measured and precise flow rate.

29 Claims, 3 Drawing Sheets

DOUBLE FEED PERISTALTIC PUMP

This application is a continuation of application Ser. No. 07/994,148, filed Dec. 21, 1992.

FIELD OF THE INVENTION

This invention relates generally to a peristaltic pump and more particularly, to a peristaltic pump having dual feed capabilities to allow the simultaneous pumping of two distinct fluids at a measured and precise flow rate.

BACKGROUND OF THE INVENTION

With the explosive growth in the biotechnology and medical technology fields and the ever increasing emphasis on accuracy and efficiency within these burgeoning technologies, a need was created for a device that could transfer precisely measured amounts of fluid. Thus, the peristaltic pump, a mechanism for moving fluids through a flexible tube was developed and has become well known in the art, particularly in the biotechnical and medical fields and in connection with analytical instruments and detectors, as well as in other fields.

Peristaltic pumps typically include engagement mechanisms rotatably mounted on a shaft so that rotation of the shaft causes the engagement mechanisms to move in a defined circular path where the engagement mechanism is intermittently brought into pressure contact with a flexible length of tubing to compress and re-compress the tubing and thereby force liquid through the tubing. Typical peristaltic pump arrangements handle a single tube at a time.

Attempts have been made to use peristaltic pumps to effect the blending or dispensing of different solutions. These attempts have brought to the surface problems with prior art peristaltic pumps, particularly when two or more different fluids are desired to be mixed in predetermined measured amounts. At times it is desired to provide precisely the same flow through two or more peristaltically pumped tubes. Calibration of a series of independently operated peristaltic pumps, particularly when the same flow rates are desired, is extremely difficult and time consuming.

Another problem associated with prior art peristaltic pumps has been the undesirable pulsation of the fluid as it is moved through the pump to its desired location. This is extremely undesirable where a steady flow rate of the desired fluids is required, such as in proportional dispensing or blending of nutrient solutions. Undesirable pulsation can lead to accuracy reduction.

A drawback of some prior art peristaltic pumps occurs with pumps which require feeding of a free end of the tube in and through an opening in the pump. This is not possible when the tube is connected at its ends, such as to a source of fluid and to the receiver to which the fluid is to be pumped. Peristaltic pumps of this type require the operator to plan ahead so the tube is fed through the pump before connections are completed or to disconnect the tube from the source or the receiver, which is time consuming and leads to possible contamination of the pumping system.

Still another drawback of prior art peristaltic pumps is the need for individual drive means or motors for each peristaltic pump when more than one peristaltic pump is employed in a given operation. Adding pumps increases the cost of equipment, torque and power and increases the space required. For example, it has now been appreciated that having a dual dispensing channel device will require less torque than that needed for two single channel pumps run by the same motor.

Finally, there has been a tendency in prior art peristaltic pumps for the flexible tubing to "walk" or move longitudinally through the pump while the pump is being driven by the external motor or other driving device. Spring loaded locks and similarly operating devices have been employed in the past in an effort to prevent such walking; however, such devices are relatively complex and require manual adjustment each time a tube of a different diameter is placed into the peristaltic pump.

It is therefore a general object of the present invention to provide an improved peristaltic pump for moving fluids through flexible tubing.

It is a further object of the present invention to provide an improved peristaltic pump for moving fluid through a flexible tube that has increased accuracy when compared with pumps having fewer engagement mechanisms rotated within the pump.

Still another object of the present invention is to provide a single peristaltic pump that will dispense fluid through two flexible tubes disposed in two independent pathways where the fluid moving through each flexible tube has precisely the same flow rate for identical tubes, or if tubes are used which have different internal diameters, the resulting flow rates are proportional to the cross-sections of the respective tubes used.

Another object of this invention is to provide a dual pumping device which requires less torque than that needed for two separate pumps run by a single motor and handling the same tubes and fluids as can be handled by the dual channel device of this invention, thereby allowing a less powerful motor to drive the dual channel device than is required to drive two single-channel peristaltic heads run from a single motor.

It is yet a further object of the present invention to provide a peristaltic pump that allows a series of pumps to be mounted piggyback on a single motor drive unit.

Yet another object of the present invention is to provide an improved peristaltic pump having a holding means that prevents the flexible tube from walking while the pump is activated and that automatically and passively accommodates tubing of differing diameters.

Another object of this invention is to provide a dual channel peristaltic pump which is suitable for biotech applications, such as "bleeding/feeding" bioreactors or fermentors, wherein an equal amount of nutrient solution needs to replace what is removed during harvesting or sampling.

Another object of the present invention is to provide a peristaltic pump suitable for one or more uses such as sample introduction into analytical instruments and detectors, proportional dispensing or blending of nutrient solutions, multiple dosing, liquid extraction or sample enrichment procedures, color blending of paints and inks, proportional pumping of plating bath additives, plating bath replenishment, water purification, for example where dispensing of chlorine or of purifiers is necessary, effluent sampling in waste water or sewage treatment, maintaining proper pH or other ion values, preparative liquid chromatography applications, such as producing step gradients having differing ratios of different buffers, high precision, high accuracy liquid metering, pharmaceutical production or dispensing, computer disk manufacturing for example dispensing slurries in the final production step of hard disk drives, enrichment of milk and other beverages, dispensing fuel oil additives, fluid sampling, fluid control, brewery addition and blending, supplementing livestock feed, medical diagnostic production, medical research metering, production line dispensing, reagent control, metering or dispensing for plastics production, and recirculation pumping.

These and other objects, advantages and features of the present invention will become apparent from the following description of the preferred embodiments of the present invention considered in conjunction with the accompanying drawings.

SUMMARY OF THE INVENTION

The improved peristaltic pump of the present invention overcomes the deficiencies of the prior art and effectively provides a peristaltic pump having dual feed mechanisms for moving fluids through a flexible tube.

The peristaltic pump according to the present invention includes a housing and a roller assembly mounted for rotation in the housing for engaging and compressing one or more flexible tubes. The peristaltic pump further includes first and second shoe members for holding the flexible tube in contact with the roller assembly, with the shoe members movably mounted to the pump in a manner whereby the shoe members move in generally opposite directions by a levered cam assembly to move them between an open mode to allow tubes to be inserted into the pump and a closed or operational mode at which fluids can be pumped through the tubes. Preferred cam assembly includes a cam shaft rotatably mounted to the housing and a first cam eccentrically mounted on the cam shaft which slidably engages the first shoe member. The cam assembly further includes a second cam mounted generally diametrically opposite the first cam on the cam shaft and operatively connected to the second shoe member, such as through a cam plate. The peristaltic pump preferably further includes forked members disposed on one or both of the shoe members to assist in holding the flexible tubing during operation of the peristaltic pump.

For a more complete understanding of the present invention, reference is now made to the embodiments illustrated in greater detail in the accompanying drawings and described below by way of example. It should be understood that the invention is not necessarily limited to the particular embodiments illustrated herein but is defined by the appended claims.

DETAILED DESCRIPTION OF PREFERRED EMBODIMENTS

Figure 1:
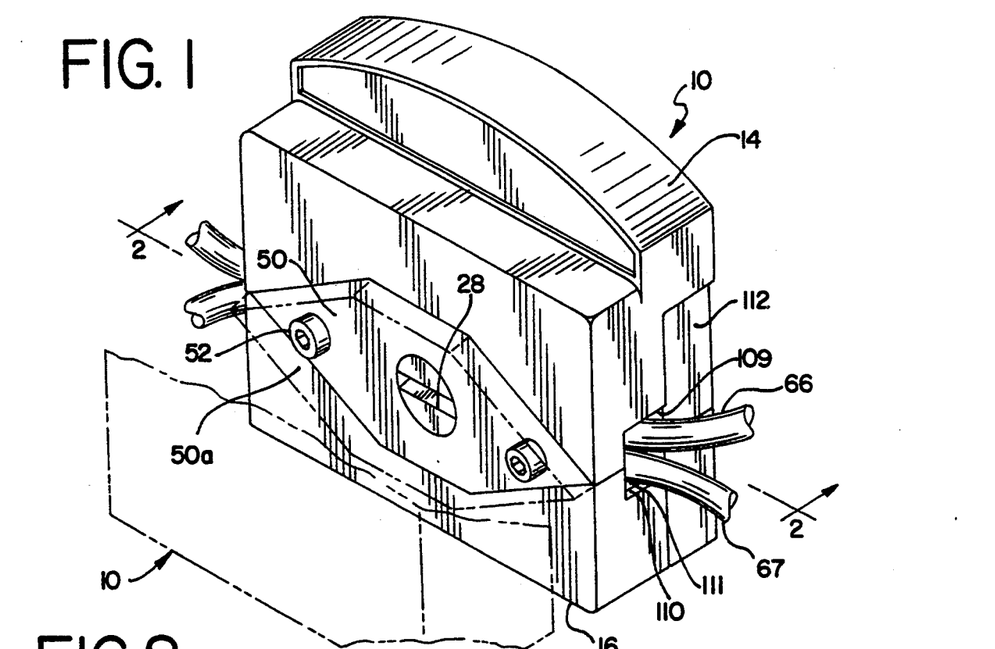
FIG. 1 is a perspective view of a peristaltic pump made according to the present invention.

A peristaltic pump made according to the present invention, generally designated as 10, is shown in FIG. 1 as including several principal parts. As perhaps best shown in FIG. 3, the peristaltic pump 10 includes a housing 12, first means for engaging a flexible tube in the form of an upper pump shoe 14, second means for engaging a flexible tube in the form of a lower pump shoe 16, a roller assembly 18 and a cam assembly 20.

Figures 3, 4:
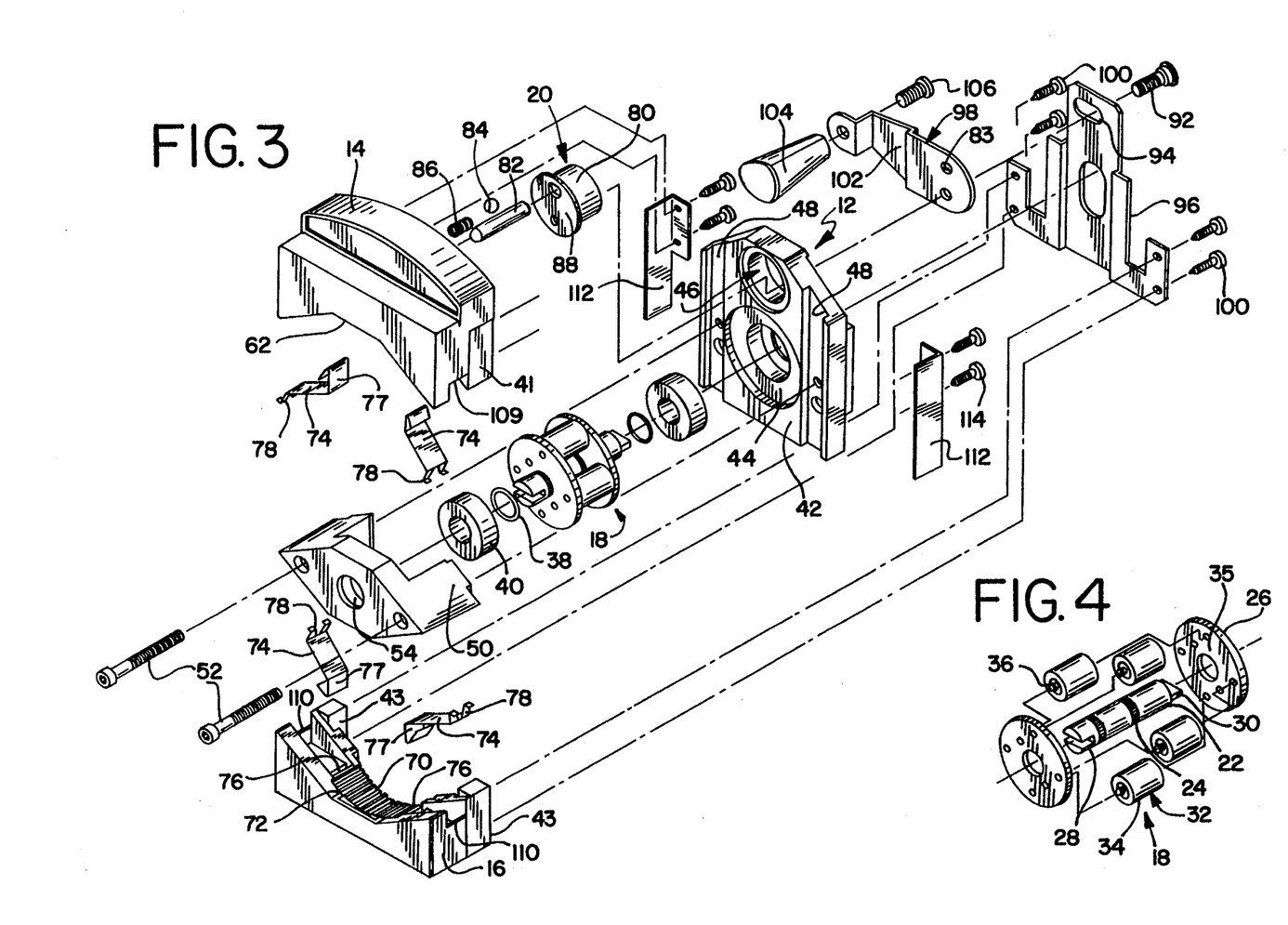
FIG. 3 is an exploded perspective view of the peristaltic pump of FIG. 1.
FIG. 4 is an exploded perspective view of the roller assembly shown in FIG. 3.

The roller assembly 18 shown in FIG. 4 includes a generally cylindrical roller assembly shaft 22. Roller shaft 22 includes two spaced apart annular knurled sections 24 adapted to provide an area for connecting generally circular roller assembly plates 26. The roller assembly plates 26 are connected to the roller shaft 22 about the knurled section 24 such that the roller assembly plates are coaxial with the roller shaft 22. Roller assembly shaft 22 further includes a groove 28 on one end and a generally rectangular drive flange 30 on the opposite end. It should be understood that the groove 28 is complementary to the drive flange 30 such that, as described in greater detail hereinafter a series of pumps 10 may be placed side by side with the flange 30 of one pump engaging and entering into the groove 28 of another pump 10 to link the two pumps and permit them to be driven by a single motor. A number of pumps 10 may therefore be placed side by side and driven by a single motor. Alternatively, other complementary ends may be utilized on the roller assembly shaft 22 to effect the linking of pumps in this general manner.

Spaced about the roller assembly shaft 22 and connected to the roller assembly plates 26 are roll and bearing assemblies 32. Advantageously, the roll and bearing assemblies 32 are equally spaced circumferentially about the shaft 22, and an even number of roll and bearing assemblies 32 are utilized so that the flexible tubes in either of the two pathways described below will be contacted simultaneously during operation of the pump 10. It is preferred that four roll and bearing assemblies 32 are equally spaced circumferentially about the roller shaft 22 and connected at either end to the roller assembly plates 26.

Each roll and bearing assembly 32 includes a base 34 mounted for rotation on a shaft 36 wherein the shaft 36 is fixedly attached at either end between the roller assembly plates 26 to allow the base 34 to rotate about the roll and bearing assembly shaft 36. The outer circumferential surface of each base 34 extends slightly radially beyond the outer edge 35 of the roller assembly plates 26 to allow the bases 34 to intermittently engage the flexible tubing. It should also be understood that when the roller assembly shaft 22 is driven, the bearing assemblies 32 rotate about the roller assembly shaft 22.

The roller assembly 18 typically further includes a pair of washers 38 disposed about either end of roller assembly shaft 22 and bearings 40 disposed on either end of the roller assembly shaft 22 adjacent the roller assembly plates 26. Roller assembly 18 is mounted for rotation in the housing 12 and is rotated by an electric motor or other conventional driving mechanism (not shown) engaging and turning the roller assembly shaft 22 in a manner generally known in the art.

The housing 12 has a pump base or body portion 42 which is a generally planar section having a bearing 44 for receiving the roller assembly 18 and a cylindrical cam bearing 46. In addition, the pump base or body 42 is provided with a pair of vertical channels 48 adapted to guide the upper pump shoe 14 and the lower pump shoe 16. Typically, the pump base or body 42 is made of aluminum or other materials of adequate strength, such as high performance polymers.

One end of the roller assembly 18 is positioned in bearing 44 of the pump base or body 42 while the other end of the roller assembly 18 is positioned in front bearing block 50. Front bearing block 50 includes a bearing 40 adapted to receive roller assembly 18. Front bearing block 50 is attached to the pump base 42 by a pair of threaded screws 52 or other suitable fastening arrangements. In addition, front bearing block 50 has an opening 54 so that roller assembly shaft 22 can extend therethrough. This allows access to the groove 28 on the roller assembly shaft 22 which may be used in conjunction with a drive flange 30 of an additional roller assembly shaft 22 to couple multiple peristaltic pumps together to be driven by a single motor, for example.

Figure 2:
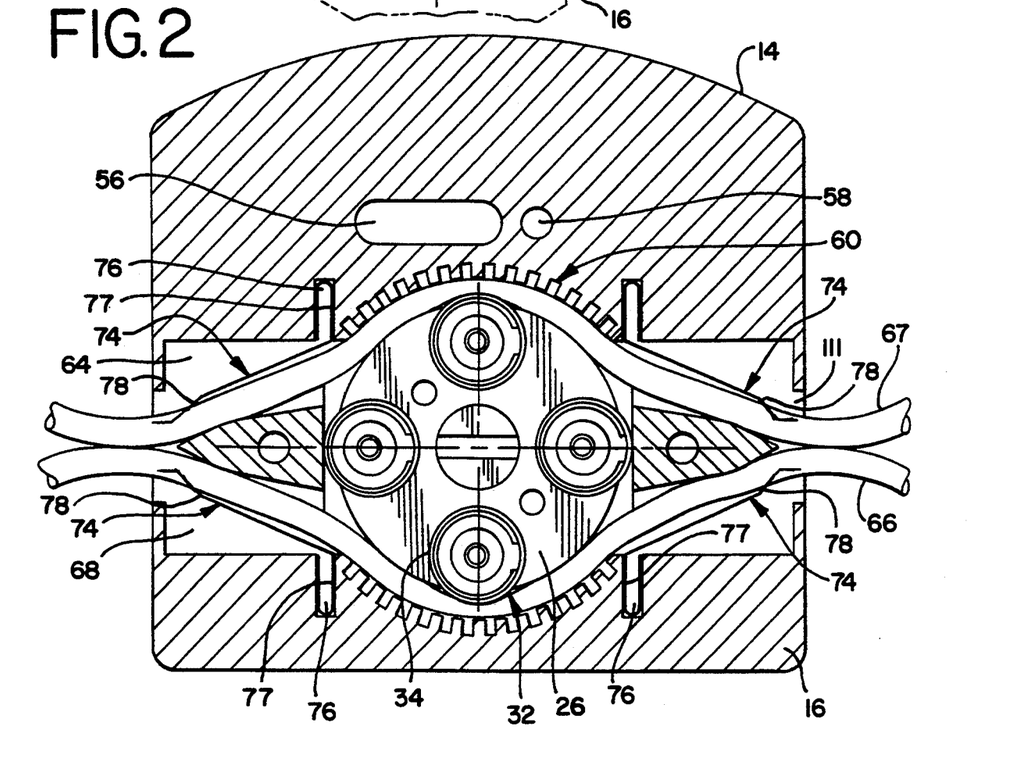
FIG. 2 is a sectioned view of the peristaltic pump of FIG. 1, taken along line 2—2 illustrating the roller assembly and two pathways.

Upper pump shoe 14 of the peristaltic pump 10 rides in the channels 48 formed in the pump body 42. In the illustrated embodiment, the shoe 14 has a pair of rails 41 sized, shaped and positioned to be slidably received in the channels 48. The upper pump shoe 14, being slidably mounted on the pump body 42, cooperates with the pump body 42 and the roller assembly 18 to form a first or upper pathway 64 through the pump 10 bound by the upper pump shoe 14, the pump body 42, the front bearing block 50 and the roller assembly 18, as shown in FIG. 2. The upper pump shoe 14 preferably includes a slot 56 and a cylindrical bore spring seat 58. Upper pump shoe 14 preferably also includes a generally arcuate ribbed section 60 generally centrally positioned along its lower edge 62 and having a curvature that is generally complementary to the path of revolution of the outside surfaces of the roll and bearing assemblies 32. Generally arcuate ribbed section 60 and the revolving roll and bearing assemblies 32 generally define the central portion of the first pathway 64. The ribbed configuration of the section 60 assists in preventing longitudinal movement of a flexible tube 66 which is within the pathway 64 during operation of the pump 10.

Lower pump shoe 16 is slidably moveable in the channels 48 of the pump body 42, typically by way of a pair of rails 43. Shoe 16 cooperates with the pump body 42 and the roller assembly 18 to form a second or lower pathway 68 through the pump 10 that is bound by the lower pump shoe 16, the pump body 42, the front bearing block 50 and the roller housing assembly 18, as shown in FIG. 2. The lower pump shoe 16 also preferably includes a generally arcuate ribbed section 70 generally centrally positioned along its upper edge 72 and having a curvature generally complementary to the arcuate path of revolution defined by the outside surfaces of the roll and bearing assemblies 32 as they revolve about the shaft 22. Generally arcuate ribbed section 70 and the revolving roll and bearing assemblies 32 generally define the central portion of the second pathway 68.

Figure 5:
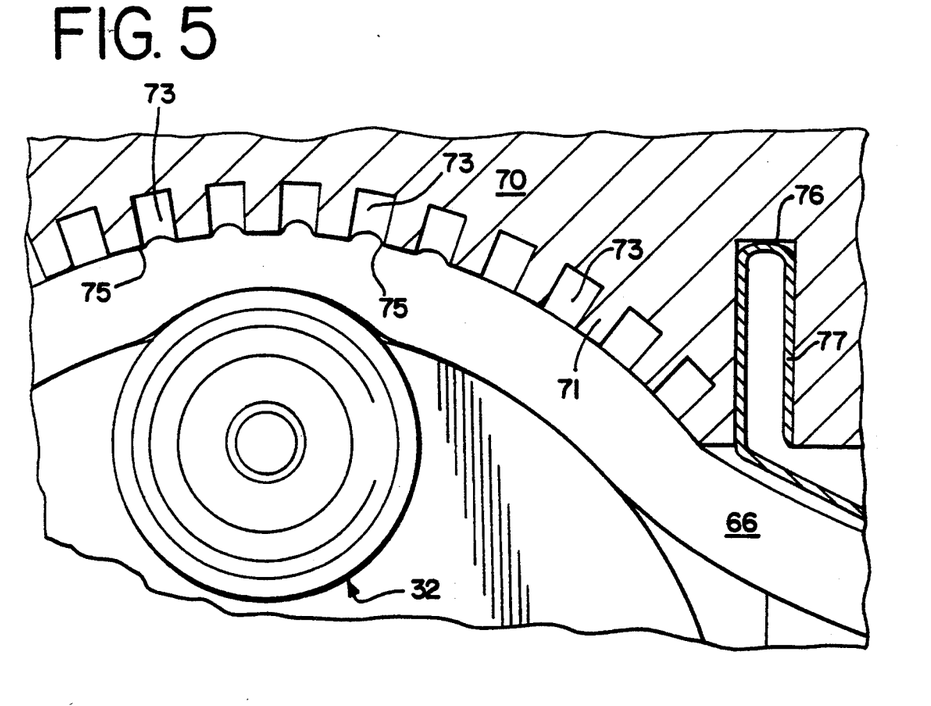
FIG. 5 is an enlarged detail view of a portion of FIG. 2.

The ribbed configuration of the section 70 assists in preventing longitudinal movement of a flexible tube 67 which is positioned within the pathway 68 during operation of the pump and reduces the compression force necessary to pinch off or seal the pump tube within the pathway. This, in turn, also reduces the torque requirement of the motor driving the pump. With reference to FIG. 5, ribbed section 70 includes a plurality of ribs 71 and grooves 73 which preferably define spaced, generally right-angled edges 75. In the illustrated embodiment, the ribs 71 and grooves 73 are generally square-shaped in elevation, as illustrated in FIG. 5. These preferred right-angled edges 75 optimize the tube retaining attributes of the device. More specifically, the tube 66, 67 is pressed into the right-angled edges 75 and is compressed between the outside surface of the ribs 71 and the working surface of the roller and bearing assembly 32, while also deforming slightly so as to have a surface portion of the tube 66, 67 bulge and enter into one or more of the grooves 73. This action continues while the pump is in operation and results in a significant reduction in the experience of tube "walking" when compared with devices having a smooth or non-ribbed opposing surface and even when compared with devices having an opposing surface that has a ribbed configuration which does not embody the right-angled edge feature.

The upper pump shoe 14 and the lower pump shoe 16 each include perimeter openings 109, 110 (FIGS. 1 and 3) that cooperate when the upper pump shoe 14 and the lower pump shoe 16 are in a closed position to form an aperture 111 that allows the tubes 66, 67 to access the first and second pathways, respectively. It should be understood that use herein of the terms upper and lower with respect to components such as the shoes is not necessarily limiting as they may be oriented in a variety of ways, for example being a right shoe and a left shoe or any other arrangement of opposing shoes or the like.

Tube holding forks 74, (FIGS. 2, 3 and 6) are disposed at either end of the pathways 64 and 68. One end 79 of each tube holding fork 74 is situated in a groove 76 in each shoe 14, 16. Each tube holding fork 74 includes a free end 78 adapted to contact the flexible tube 66, 67 when it is displaced in its respective pathway 64, 68 and hold the flexible tube 66, 67 in such a way that operation of the peristaltic pump, causing any longitudinal movement or "walking" of the flexible tube not already prevented by the ribbed configuration of the pump shoe 14, 16, will pull the tube 66, 67 into the holding fork 74 until a firm engagement or seat is achieved. Preferably, each fork 74 is generally V-shaped at portion 77 to effectively engage the flexible tube 66, 67. It is preferred that the tube holding forks 74 be made of a spring quality stainless steel or similar material which will durably impart a biasing force onto the flexible tube 66, 67. Due to the inherently resilient nature of the tube holding forks 74, the tube holding forks 74 automatically engage the flexible tube 66, 67 and bias it toward the front bearing block. This engagement has a passive characteristic and typically requires no adjustment when tubing sizing is changed.

Figure 6:
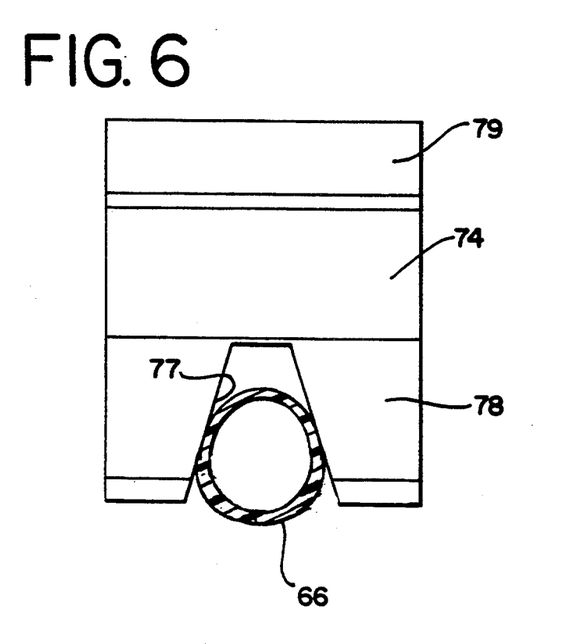
FIG. 6 is an end elevational view of a tube holding fork in its engagement with a flexible tube.

It should be understood that the tube holding forks are preferably provided in pairs on each shoe, to prevent the flexible tubes 66, 67 from walking, although in some circumstances single forks may be sufficient. When two flexible tubes 66, 67 are utilized, the flexible tubes are biased against the bearing block cap 50 and each other by the tube holding forks to prevent walking. In addition, the tube holding forks may be easily removed from and inserted into the shoes to permit the substitution of tube holding forks with differently spaced tines to accommodate various size flexible tube, in the event differently sized or spaced tines might be needed.

Cam assembly 20 includes a cylindrical cam shaft 80 positioned for rotation in pump cam bearing 46 in the upper portion of the pump body 42. The cam shaft 80 has an eccentrically mounted upper shoe cam 82 that extends into the slot 56 in the top portion of the upper shoe 14. A cam ball 84 and a cam spring 86 are provided to be seated in a cylindrical bore 88 in the cam shaft 80 and in corresponding cylindrical bore spring seat 58 in the upper pump shoe 14 when the pump is closed.

A lower shoe cam 92 is eccentrically mounted diametrically opposite and on the opposite face of the cam shaft 80 to transfer rotational movement of the cam shaft 82 into translational movement of the lower pump shoe 16. The lower shoe cam 92 is inserted through a slot 94 in a lower cam plate 96 and a pump lever 98. The lower cam plate 96 is suitably mounted such as by screws 100 to the lower pump shoe 16. The pump lever 98 is generally a narrow plate section 102 having a gripping member such as knob 104 and a pump stud 106 or the like for securing the pump knob 104 to the plate section 102.

Cam ball 84 and cam spring 86 help retain the cam assembly in the closed or locked position. As pump lever 98 is rotated 180 degrees, the cams typically have moved about 2 degrees beyond the centerline of the pump body such that the resulting back pressure from the compressed flexible tubes will "lock" the cams against the mechanical stop of lever 98. In this position of the cam assembly, the cam ball 84 will engage into the cylindrical bore of cam shaft 80.

The upper shoe cam 82 when positioned in cam shaft 80 extends slightly outwardly from the opposite face of the cam shaft 80 providing a boss for engaging a hole 83 in the plate section 102 of the pump lever 98 for securing the pump lever 98 to the cam shaft 80. It should be understood that the lower shoe cam 92 is eccentrically mounted to the pump lever 98. In addition the pump 10 may be provided with pump brackets 112 attached by screws 114 or the like to the upper pump shoe 14 to help maintain proper positioning of the shoes 14, 16 during operation of the pump.

In operation, it is first necessary to insert one or more flexible tubes into the first and/or the second pathways. In order to insert flexible tubing 66, 67 into the peristaltic pump 10, the pump lever 98 should be at the position as shown in FIG. 3. In this position, the peristaltic pump is generally open; that is, the upper shoe cam 82 is at its maximum upward vertical position and the lower shoe cam 92 is at its maximum downward vertical position. When the lever 98 rotates the cam shaft 80 and hence the upper shoe cam 82 to its position shown in FIG. 3, the upper shoe 14 moves vertically upwardly while guided by the channels 48 of the pump body 42. This rotation of the cam shaft 80 also simultaneously rotates the lower shoe cam 92 moving the cam plate 96 and the lower shoe 16 vertically downwardly while being guided by in the channels 48 of the pump body 42. This movement of the upper and lower shoes generally away from each other maximizes the width of the first and second pathways allowing flexible tubing 66 and/or 67 to be placed into the first and/or second pathways. It should be noted that the width of the first and second pathways is great enough such that the flexible tubing need not be threaded longitudinally into the pump 10 through the opening 110 in the pump 10; rather, an entire portion of the tubing may be aligned adjacent the pathways and then laterally placed or pushed all at once into the pathways.

Once flexible tubing 66, 67 is thus positioned, the pump lever 98 is rotated 180° from its position in FIG. 3 which causes the upper shoe cam 82 to move the upper pump shoe 14 vertically downwardly and simultaneously causes the lower shoe cam 92 and cam plate 94 to move the lower pump shoe 16 vertically upwardly. Such movements decrease the width of the first and second pathways and cause the generally arcuate portion 60 of the upper pump shoe 14 to engage the flexible tubing 66 in the first pathway 64 and the generally arcuate portion 70 of the lower pump shoe 16 to engage the flexible tube 66 in the second pathway 68. In this closed position, the drive means (not shown) for the roller assembly 18 may be activated to rotate the roller assembly 18 and its circumferentially spaced roll and bearing assemblies 32. The roll and bearing assemblies 32 rotate and thereby simultaneously intermittently contact and compress the flexible tube 66 in the first pathway 64 between the rotating roll and bearing assemblies 32 and the upper pump shoe 14 and the flexible tube 67 in the second pathway 68 between the rotating roll and bearing assemblies 32 and the lower pump shoe 16, forcing fluid in each of the flexible tubes to move through the tube in a manner known to be characteristic of a peristaltic pump.

It should be noted that the fluid flowing through the flexible tube in the first pathway 64 will move in one direction while the fluid moving through the flexible tube disposed in the second pathway 68 will move in the opposite direction. Pump 10 therefore allows an operator to pump two different fluids having the exact same flow rate through different pathways utilizing a single motor and a single peristaltic pump 10, provided the respective tubes have the same diameter sizes and flexibility properties and provided the respective fluids have the same or similar properties such as viscosity.

Should it be desirable to pump more than two fluids simultaneously, a series of pumps 10 may be stacked and utilized and driven by a single motor. In this regard an alternate embodiment is shown in phantom in FIG. 1. It will be noted the front bearing block 50 extends laterally beyond the upper and lower shoe a predetermined distance, and one or more additional pump assemblies 10' are mounted thereto by extra length screws 52. It is preferred that the predetermined distance be at least equal in length to the diameter of the flexible tube thereby allowing respective upper and or lower shoes to be placed "piggyback" or side-by-side while still allowing access for the flexible tubing to be placed in multiple first and/or second pathways. Multiple roller assemblies 18 will also be provided, and groove 28 from one roller assembly and drive flange 30 from another roller assembly cooperate to link any number of pumps 10 when placed side-by-side. Also, suitable means are provided to move the shoes as needed and as generally described herein.

It will thus be seen that the present invention provides a new and useful peristaltic pump having dual pathways which has a number of advantages and characteristics including those pointed out herein and others which are inherent in the invention. The preferred embodiment of the invention having been described by way of example, it is anticipated that modifications may be made to the described form without departing from the spirit of the invention or the scope of the appended claims.

What is claimed is:

1. A peristaltic pump comprising:
   a housing;
   roller means mounted for rotation with respect to said housing for engaging and compressing first and second portions of flexible tubing;
   a cam assembly mounted with respect to said housing;

first and second shoe means for holding the respective first and second portions of flexible tubing in contact with said roller means, said first shoe means movably mounted with respect to said housing and moveable in a first direction by said cam assembly to engage the first portion of flexible tubing with said roller means and in a second direction generally opposite said first direction to disengage the first portion of flexible tubing from said roller means and permit removal of the first portion of flexible tubing from said pump, said second shoe means movable in said second direction by said cam assembly to engage the second portion of the flexible tubing with said roller means and in said first direction to disengage the second portion of flexible tubing from said roller means and permit removal of the second portion of flexible tubing from said pump;

a forked member disposed on at least one of said first and second shoe means, said forked member biasing one of the portions of flexible tubing against a generally rigid member of the pump when the flexible tube is disposed in said pump, and;

said forked member has a generally V-shaped end portion which engages one of the portions of flexible tubing, whereby said portion of tubing is pulled, by the action of the pump, into firm engagement with the V-shaped end portion.

2. A peristaltic pump comprising:

a pump housing having a bearing block member secured thereto;

roller means rotatably mounted on said housing, said roller means adapted to engage and compress flexible tubing to cyclically displace measured amounts of fluid through said tubing;

a first pathway for a first flexible tube defined by a first shoe movable with respect to said housing, said roller means and said bearing block member;

a second pathway for a second flexible tube defined by a second shoe movable with respect to said housing, said roller means and said bearing block member;

drive means mounted in said pump housing to drive said first shoe in a first direction to a closed position to engage a portion of said first flexible tube with said roller means when said first flexible tube is disposed in said first pathway and in a second direction opposite said first direction to disengage said first flexible tube from said roller means and permit removal of the first flexible tube from said pump, said drive means driving said second shoe in said second direction to a closed position to engage a portion of said second flexible tube with said roller means when said second flexible tube is disposed in said second pathway and in said first direction to disengage said second flexible tube from said roller means and permit removal of said second flexible tube from said pump;

a fork member disposed on at least one of said first and second shoes for holding said respective first and second flexible tubes against a portion of said bearing block member to prevent longitudinal movement of at least one of said first and second flexible tubes; and each of said shoes has a generally arcuate ribbed section having a plurality of ribs alternating with a plurality of associated grooves to define a plurality of right-angled edges, each of said ribs, grooves and edges being generally transverse to of the flexible tubing.

3. A peristaltic pump comprising:

a housing;

roller means mounted for rotation with respect to said housing for engaging and compressing first and second portions of flexible tubing;

a cam assembly mounted with respect to said housing;

first and second shoe means for holding the respective first and second portions of flexible tubing in contact with said roller means, said first shoe means movably mounted with respect to said housing and moveable in a first direction by said cam assembly to engage the first portion of flexible tubing with said roller means and in a second direction generally opposite said first direction to disengage the first portion of flexible tubing from said roller means and permit removal of the first portion of flexible tubing from said pump, said second shoe means moveable in said second direction by said cam assembly to engage the second portion of the flexible tubing with said roller means and in said first direction to disengage the second portion of flexible tubing from said roller means and permit removal of the second portion of flexible tubing from said pump; and said cam assembly includes a cam shaft rotatably mounted in a circular bearing in said housing, a first cam eccentrically mounted on said cam shaft and slidably engageable with said first shoe means, and a second cam mounted generally diametrically opposite said first cam on said cam shaft and connected to said second shoe means.

4. The peristaltic pump of claim 3 wherein said roller means includes a pump linking means for linking a series of adjacent pumps.

5. A peristaltic pump comprising:

a pump housing having a bearing block member secured thereto;

roller means rotatably mounted to said housing, said roller means adapted to engage and compress flexible tubing to cyclically displace measured amounts of fluid through said tubing;

a first shoe movably mounted with respect to said housing to permit displacement of said first shoe in a first direction to engage a first portion of flexible tubing with said roller means and in a second direction to disengage the first portion of flexible tubing from said roller means and permit removal of the first portion of flexible tubing from said pump;

a second shoe movable with respect to said housing to permit displacement of said second shoe in said second direction to engage a second portion of the flexible tubing with said roller means and in said first direction to disengage the second portion of flexible tubing from said roller means and permit removal of the second portion of flexible tubing from said pump;

means for simultaneously moving said first and second shoes to engage said respective first and second portions of the flexible tubing with said roller means;

a first pathway on one side of said pump generally defined by said first shoe, said roller means and said bearing block member; and a second pathway on an opposing side of said pump generally defined by said second shoe, said roller means, and said bearing block member; and each of said shoes has a generally arcuate ribbed section having a plurality of associated grooves to define a plurality of right-angled edges, each of said ribs, grooves and edges being generally transverse to the flexible tubing.

6. The peristaltic pump of claim 5 wherein said roller means includes a pump linking means for linking a series of adjacent pumps.

7. A peristaltic pump comprising:

a housing;

roller means mounted for rotation with respect to said housing for engaging and compressing first and second portions of flexible tubing;

a cam assembly mounted with respect to said housing;

first and second shoe means for respectively holding the first and second portions of flexible tubing in contact with said roller means, said first shoe means movably mounted with respect to said housing and moveable in a first direction by said cam assembly to engage the first portion of flexible tubing with said roller means and in a second direction generally opposite said first direction to disengage the first portion of flexible tubing from said roller means and permit removal of the first portion of flexible tubing from said pump, said second shoe means moveable in said second direction by said cam assembly to engage the second portion of the flexible tubing with said roller means and in said first direction to disengage the second portion of flexible tubing from said roller means and permit removal of the second portion of flexible tubing from said pump; and at least one of said shoe means includes a generally arcuate ribbed section which engages one of said respective first and second portions of flexible tubing, and said generally arcuate ribbed section includes at least one rib and at least one groove which define a right-angled edge, whereby the respective first and second portions of flexible tubing is pressed into the right-angled edge and forms a bulge in the flexible tubing which enters into said groove.

8. The peristaltic pump of claim 7, wherein both of said shoe means includes said generally arcuate ribbed section and wherein both of said generally arcuate ribbed sections have a plurality of said ribs, grooves and right-angled edges.

9. The peristaltic pump of claim 7 wherein said roller means includes a pump linking means for linking a series of adjacent pumps.

10. A peristaltic pump comprising:

a pump housing having a bearing block member secured thereto;

roller means rotatably mounted from said housing, said roller means adapted to engage and compress flexible tubing to cyclically displace measured amounts of fluid through said tubing;

a first pathway for a first flexible tube defined by a first shoe movable with respect to said housing, said roller means and said bearing block member;

a second pathway for a second flexible tube defined by a second shoe movable with respect to said housing, said roller means and said bearing block member;

drive means mounted in said pump housing to drive said first shoe in a first direction to a closed position to engage a portion of said first flexible tube with said roller means when said first flexible tube is disposed in said first pathway and in a second direction opposite said first direction to disengage said first flexible tube from said roller means and permit removal of the first flexible tube from said pump, said drive means driving said second shoe in said second direction to a closed position to engage a portion of said second flexible tube with said roller means when said second flexible tube is disposed in said second pathway and in said first direction to disengage said second flexible tube from said roller means and permit removal of said second flexible tube from said pump;

a fork member disposed on at least one of said first and second shoes for holding said first or second flexible tube against a portion of said bearing block member to prevent longitudinal movement of at least one of said first and second flexible tubes; and said drive means includes a cam assembly having a cam shaft rotatably mounted to a circular bearing in said housing, a first cam connected to said cam shaft and slidably engageable with said first shoe and, a second cam mounted on said cam shaft and operatively connected to said second shoe.

11. The peristaltic pump of claim 10, wherein said second cam is connected to said second shoe means through a cam plate.

12. The peristaltic pump of claim 10, further including means for rotating said cam shaft.

13. A peristaltic pump comprising:

a pump housing having a bearing block member secured thereto;

roller means rotatably mounted to said housing, said roller means adapted to engage and compress flexible tubing to cyclically displace measured amounts of fluid through said tubing;

a first shoe movably mounted with respect to said housing to permit displacement of said first shoe in a first direction to engage a first portion of flexible tubing with said roller means and in a second direction to disengage the first portion of flexible tubing from said roller means and permit removal of the first portion of flexible tubing from said pump;

a second shoe moveable with respect to said housing to permit displacement of said second shoe in said second direction to engage a second portion of flexible tubing with said roller means and in said first direction to disengage the second portion of flexible tubing from said roller means and permit removal of the second portion of flexible tubing from said pump;

a unitary assembly for simultaneously moving said first and second shoes to engage said respective first and second portions of the flexible tubing with said roller means, a first pathway on one side of said pump generally defined by said first shoe, said roller means and said bearing block member; and a second pathway on an opposing side of said pump generally defined by said second shoe, said roller means, and said bearing block member.

14. The peristaltic pump of claim 13, further including a forked member disposed on at least one of said first and second shoes, said forked member respectively engaging the first and second portions of flexible tubing and biasing said respective first and second portions of flexible tubing against said bearing block member when the flexible tubing is disposed in said pump.

15. The peristaltic pump of claim 13, wherein said roller means includes an even number of equally circumferentially spaced rollers mounted for rotation about a shaft.

16. The peristaltic pump of claim 13, wherein said second direction is opposite said first direction.

17. A peristaltic pump comprising:
a pump housing having a bearing block member secured thereto;
roller means rotatably mounted to said housing, said roller means adapted to engage and compress flexible tubing to cyclically displace measured amounts of fluid through said tubing;
a first shoe movably mounted with respect to said housing to permit displacement of said first shoe in a first direction to engage a first portion of flexible tubing with said roller means and in a second direction to disengage the first portion of flexible tubing from said roller means and permit removal of the first portion of flexible tubing from said pump;
a second shoe movable with respect to said housing to permit displacement of said second shoe in said second direction to engage a second portion of flexible tubing with said roller means and in said first direction to disengage the second portion of flexible tubing from said roller means and permit removal of the second portion of flexible tubing from said pump;
means for simultaneously moving said first and second shoes to engage said respective first and second portions of the flexible tubing with said roller means, said means for simultaneously moving said first and second shoes includes a cam assembly including a cam shaft rotatably mounted to a circular bearing in said housing, a first cam connected to said cam shaft and slidably engageable with said first shoe, and a second cam mounted on said cam shaft and operatively connected to said second shoe;
a first pathway on one side of said pump generally defined by said first shoe, said roller means and said bearing block member; and
a second pathway on an opposing side of said pump generally defined by said second shoe, said roller means, and said bearing block member.

18. The peristaltic pump of claim 17, wherein said second cam is connected to said second shoe through a cam plate.

19. The peristaltic pump of claim 17, further including means for rotating said cam shaft.

20. The peristaltic pump of claim 17 wherein said roller means includes a pump linking means for linking a series of adjacent pumps.

21. A peristaltic pump comprising:
a pump housing having a bearing block member secured thereto;
roller means rotatably mounted on said housing, said roller means adapted to engage and compress flexible tubing to cyclically displace measured amounts of fluid through said tubing;
a first pathway for a first flexible tube defined by a first shoe movable with respect to said housing, said roller means and said bearing block member;
a second pathway for a second flexible tube defined by a second shoe movable with respect to said housing, said roller means and said bearing block member;
drive means mounted in said pump housing to drive said first shoe in a first direction to a closed position to engage a portion of said first flexible tube with said roller means when said first flexible tube is disposed in said first pathway and in a second direction opposite said first direction to disengage said first flexible tube from said roller means and permit removal of the first flexible tube from said pump, said drive means driving said second shoe in said second direction to a closed position to engage a portion of said second flexible tube with said roller means when said second flexible tube is disposed in said second pathway and in said first direction to disengage said second flexible tube from said roller means and permit removal of said second flexible tube from said pump;
a fork member disposed on at least one of said first and second shoes for holding said respective first and second flexible tubes against a portion of said bearing block member to prevent longitudinal movement of at least one of said first and second flexible tubes.

22. The peristaltic pump of claim 21, wherein said roller means includes a pump linking means for linking a series of adjacent pumps.

23. The peristaltic pump of claim 21, wherein said roller means includes an even number of equally circumferentially spaced bearing assemblies mounted for rotation about a shaft.

24. The peristaltic pump of claim 21, wherein said drive means simultaneously moves said first shoe and said second shoe.

25. A peristaltic pump comprising:
a housing;
roller means mounted for rotation with respect to said housing for engaging and compressing first and second portions of flexible tubing;
a cam assembly mounted with respect to said housing;
first and second shoe means for respectively holding the first and second portions of flexible tubing in contact with said roller means, said first shoe means movably mounted with respect to said housing and moveable in a first direction by said cam assembly to engage the first portion of flexible tubing with said roller means and in a second direction generally opposite said first direction to disengage the first portion of flexible tubing from said roller means and permit removal of the first portion of flexible tubing from said pump, said second shoe means moveable in said second direction by said cam assembly to engage the second portion of flexible tubing with said roller means and in said first direction to disengage the second portion of flexible tubing from said roller means and permit removal of the second portion of flexible tubing from said pump; and
a substantially resilient member disposed on one of said first and second shoe means, said substantially resilient member respectively biasing one of said first and second portions of flexible tubing against a generally rigid member of the pump.

26. The peristaltic pump of claim 25, wherein said roller means includes an even number of equally circumferentially spaced rollers mounted for rotation about a shaft.

27. The peristaltic pump of claim 25, wherein at least one of said shoe means includes a generally arcuate ribbed section which respectively engages one of the first and second portions of flexible tubing.

28. The peristaltic pump of claim 25, wherein said substantially resilient member is a forked member which respectively engages one of the first and second portions of flexible tubing, whereby said respective first and second portions of tubing is pulled, by action of the pump, into firm engagement with the forked member.

29. The peristaltic pump of claim 28, wherein said generally rigid member is a bearing block member secured to said housing.

* * * * *

UNITED STATES PATENT AND TRADEMARK OFFICE
CERTIFICATE OF CORRECTION

PATENT NO. : 5,340,290
DATED : August 23, 1994
INVENTOR(S) : Anton H. Clemens

It is certified that error appears in the above-indentified patent and that said Letters Patent is hereby corrected as shown below:

```
Col. 5, line 38, "moveable" should read --movable--.
Col. 7, line 50, delete --in--.
Col. 9, line 5, "moveable" should read --movable--.
Col. 10, line 14, "moveable" should read --movable--;
      line 21, "moveable" should read --movable--; line 36,
      "claim 3 wherein" should read --claim 3, wherein--.
Col. 11, line 9, "claim 5 wherein" should read --claim 5,
      wherein--; line 23, "moveable" should read --movable--;
      line 30, "moveable" should read --movable--; line 52,
      "claim 7 wherein" should read --claim 7, wherein--.
Col. 12, line 47, "moveable" should read --movable--.
Col. 13, line 54, "claim 17 wherein" should read --claim
      17, wherein--.
Col. 14, line 46, "moveable" should read --movable--; line
      53, "moveable" should read --movable--.
```

Signed and Sealed this

Twenty-sixth Day of September, 1995

*Attest:*

BRUCE LEHMAN

*Attesting Officer*   *Commissioner of Patents and Trademarks*